United States Patent
Riley

(10) Patent No.: US 8,217,667 B2
(45) Date of Patent: Jul. 10, 2012

(54) METHOD AND APPARATUS FOR PIEZOELECTRIC SENSOR STATUS ASSESSMENT

(75) Inventor: Carl William Riley, Milan, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 322 days.

(21) Appl. No.: 12/355,240

(22) Filed: Jan. 16, 2009

(65) Prior Publication Data

US 2010/0182025 A1 Jul. 22, 2010

(51) Int. Cl.
*G01R 27/08* (2006.01)

(52) U.S. Cl. .............. 324/691; 5/665; 5/689; 5/710; 5/713; 324/727; 73/579; 73/1.82

(58) Field of Classification Search .......... 324/691
See application file for complete search history.

(56) References Cited

U.S. PATENT DOCUMENTS

| | | | | |
|---|---|---|---|---|
| 5,524,281 A * | 6/1996 | Bradley et al. | ............ | 455/67.15 |
| 5,929,723 A * | 7/1999 | Kimura et al. | ............ | 333/193 |
| 6,531,884 B1 * | 3/2003 | Kleven | ............ | 324/727 |
| 6,819,254 B2 * | 11/2004 | Riley | ............ | 340/665 |
| 7,525,324 B2 * | 4/2009 | Ohnishi et al. | ............ | 324/727 |
| 7,596,823 B2 * | 10/2009 | Friedrichs | ............ | 5/713 |
| 7,869,903 B2 * | 1/2011 | Turner et al. | ............ | 700/275 |
| 2002/0024346 A1 * | 2/2002 | Ikuta et al. | ............ | 324/727 |
| 2003/0024298 A1 * | 2/2003 | Baber et al. | ............ | 73/1.82 |
| 2004/0074303 A1 * | 4/2004 | Matsiev et al. | ............ | 73/579 |
| 2004/0194532 A1 * | 10/2004 | Lally et al. | ............ | 73/1.82 |
| 2005/0284224 A1 * | 12/2005 | Yamada et al. | ............ | 73/579 |
| 2006/0070453 A1 * | 4/2006 | Werve | ............ | 73/800 |
| 2007/0276202 A1 * | 11/2007 | Raisanen et al. | ............ | 600/301 |
| 2008/0141463 A1 * | 6/2008 | Dionne et al. | ............ | 5/713 |
| 2008/0238259 A1 * | 10/2008 | Osawa | ............ | 310/334 |
| 2009/0056020 A1 * | 3/2009 | Caminade et al. | ............ | 5/600 |
| 2009/0177327 A1 * | 7/2009 | Turner et al. | ............ | 700/275 |
| 2010/0208785 A1 * | 8/2010 | Lindqvist et al. | ............ | 375/227 |
| 2010/0253183 A1 * | 10/2010 | Ando et al. | ............ | 310/338 |

FOREIGN PATENT DOCUMENTS

EP 327254 A1 * 8/1989
JP 2005351781 * 12/2005

OTHER PUBLICATIONS

Agilent Network Analyzer Basics, Agilent Document No. 5965-8017E, Copyright Agilent Technologies, Inc., 2004.*
M.I. Subbotin Measurement Techniques, vol. 46, No. 2, 2003 Diagnostics of Piezoelectric Sensors From the Form of Their Decaying Resonance Oscillations 2003 Plenum Publishing Corporation.

* cited by examiner

*Primary Examiner* — Timothy J Dole
*Assistant Examiner* — Benjamin M Baldridge
(74) *Attorney, Agent, or Firm* — Barnes & Thornburg LLP

(57) ABSTRACT

A method for assessing the status of a piezoelectric sensor of interest is disclosed. The sensor of interest is located adjacent a surface of a mattress supporting a person. In some instances, the sensor of interest may be coupled to a mattress or coupled to a bed frame that supports the mattress. The method involves analyzing the complex impedance of the excited sensor relative to a complex impedance profile. A system for implementing the method is also disclosed.

26 Claims, 8 Drawing Sheets

METHOD AND APPARATUS FOR PIEZOELECTRIC SENSOR STATUS ASSESSMENT

TECHNICAL FIELD

The subject matter described herein relates to a method and apparatus for assessing the status or health of a piezoelectric sensor, and particularly to a method and apparatus for assessing the health of the sensor in an installed condition.

BACKGROUND

Piezoelectric sensors are used in many applications to sense mechanical loads or movement, including vibration. One example of the use of piezoelectric sensors is in a bed for accommodating a patient in a health care facility or home care setting. The sensors may be used to reveal patient position and/or movement. The sensors may also be used to measure patient weight or to monitor physiological variables such as patient respiration and heart rate.

When used in such applications, piezoelectric sensors are integrated into a mattress or otherwise installed where they are both between and in contact with other components of the bed. As a result, the sensors may sustain damage causing them to malfunction. As a result, any information based on the sensor could be erroneous. It is, therefore, desirable to be able to assess the status of the sensors so that malfunctioning sensors can be identified and appropriate corrective action can be taken if necessary.

SUMMARY

The present application discloses a method for assessing the status of a piezoelectric sensor of interest. The method comprises the steps of 1) establishing a complex impedance profile expected to be exhibited by an acceptable sensor subjected to a test signal, 2) exciting the sensor of interest with a periodic excitation signal correlatable to the test signal, 3) analyzing the complex impedance of the excited sensor relative to the complex impedance profile, and 4) reaching a conclusion about the status of the sensor of interest based on the analysis. A system for carrying out an assessment of the status of a piezoelectric sensor of interest includes an analog signal source, a communication path for placing the signal source in communication with the sensor of interest, means for digitizing a complex impedance exhibited by the excited sensor, and a processor in communication with the A-D converter, the processor having access to a complex impedance profile representing an expected complex impedance of the excited sensor and also having access to an algorithm for analyzing digitized complex impedance relative to the complex impedance profile and for generating a status signal responsive to the analysis.

The foregoing and other features of the various embodiments of the method and apparatus described herein will become more apparent from the following detailed description and the accompanying drawings.

DETAILED DESCRIPTION

Figure 1:
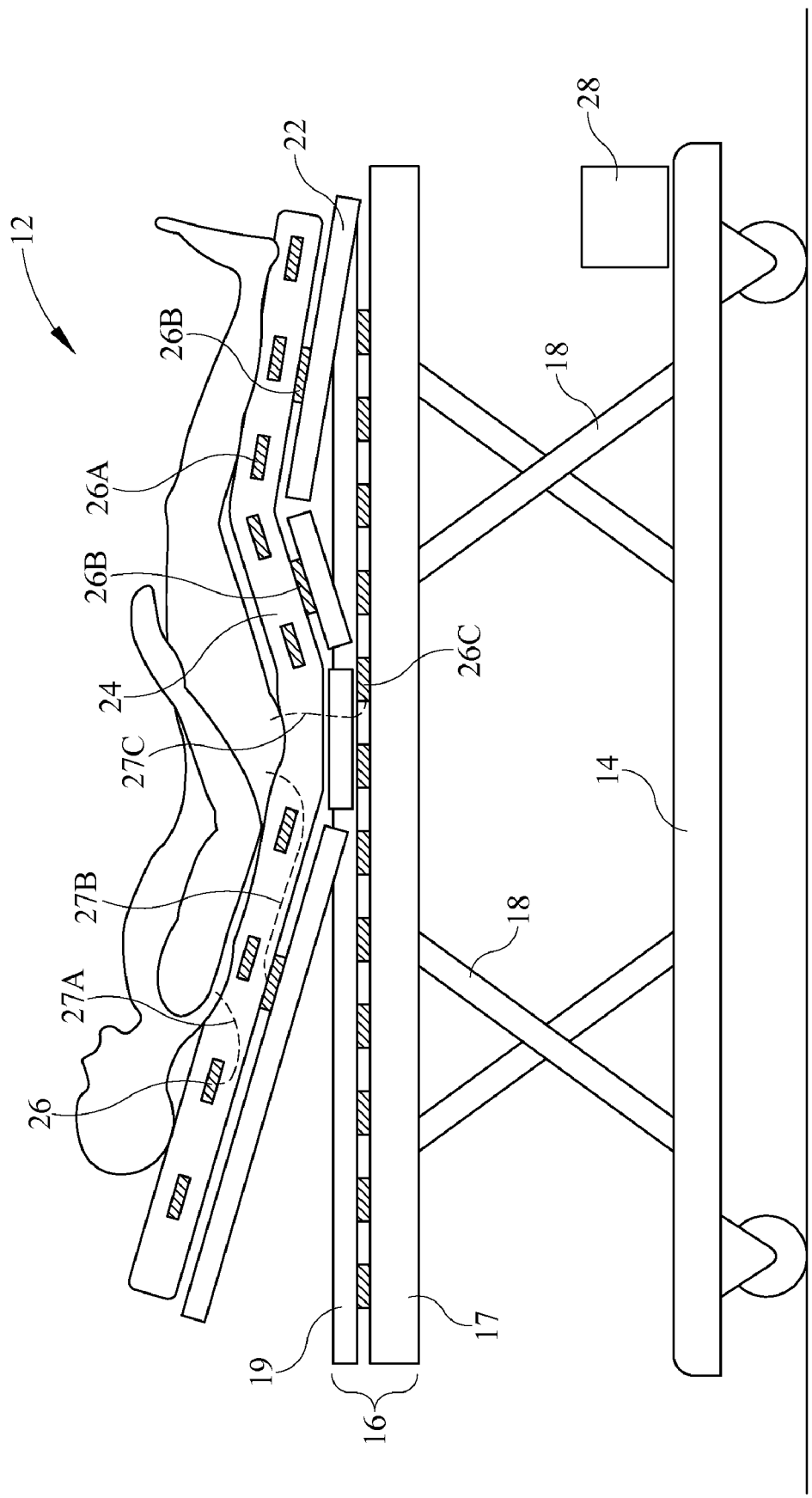
FIG. 1 is a schematic side elevation view of a bed for accommodating a patient, the bed including piezoelectric sensors and a sensor diagnostic system. The piezoelectric sensors, as depicted, are disproportionately large in comparison to the other components of the bed.

Referring to FIG. 1, a patient care bed 12 includes a base frame 14 and an elevatable frame 16 comprising a lower elevatable frame 17 and an upper elevatable frame 19. A linkage 18 connecting the elevating frame to the base frame allows the elevating frame to be raised or lowered. The bed also includes an articulable deck 22 and a mattress 24. The mattress is made at least partly of a foam material but may also include air bladders or liquid bladders.

The bed includes piezoelectric sensors generally designated as 26 and more specifically designated 26A, 26B, 26C based on their installed environment and principal intended use. Sensors 26A are embedded in and are in contact with the mattress foam. Sensors 26A are used to monitor physiological parameters of the bed occupant. Such parameters include pulse and respiration, the vibrations of which are conveyed from the patient to the sensors 26A by way of the foam. Sensors 26B reside between and are in contact with the mattress and the deck. Sensors 26B are used to determine the occupant's weight. Sensors 26C reside between and are in contact with the upper and lower elevatable frames. Sensors 26C are used to monitor weight distribution and therefore patient position and/or movement. As seen in the Figure, each type of sensor (26A, 26B, 26C) is coupled to the occupant by way of a path (27A, 27B, 27C) traversing through solid phase material (e.g. the foam of the mattress and the metal or plastic material of the deck and upper frame) or liquid phase material (e.g. water in any fluid bladders) without crossing into a substantially gaseous phase material (e.g. an air filled bladder or an air satisfactory signal coupling (e.g. minimal signal attenuation) between the sensors and the occupant.

If a piezoelectric sensor is excited by a periodic electrical signal, and if no external force is applied to the sensor, the sensor will deflect back and forth at the same frequency and relative amplitude as the applied signal. If an external force is applied while the electrical signal is applied, the external mechanical force will inhibit the electrically induced motion of the sensor. This resistance to motion will be reflected back to the electrical circuit as an impedance to current flow, and the applied electrical energy not manifested as motion will be dissipated as heat. The electrical circuit can include means for detecting this change in impedance, for example, by monitoring changes in current flow or, in a constant current system, by changes in voltage across the piezoelectric sensor. As taught herein, the impedance-frequency characteristic of a piezoelectric sensor in contact with surrounding structure, and therefore, subject to external constraints, exhibits a complex impedance with defining characteristics. These characteristics change as a result of damage sustained by the sensor. For example the frequency corresponding to a resonant peak may be displaced to a higher or lower frequency. Such changes can be used to assess the health or status of a piezoelectric sensor.

Figure 2:
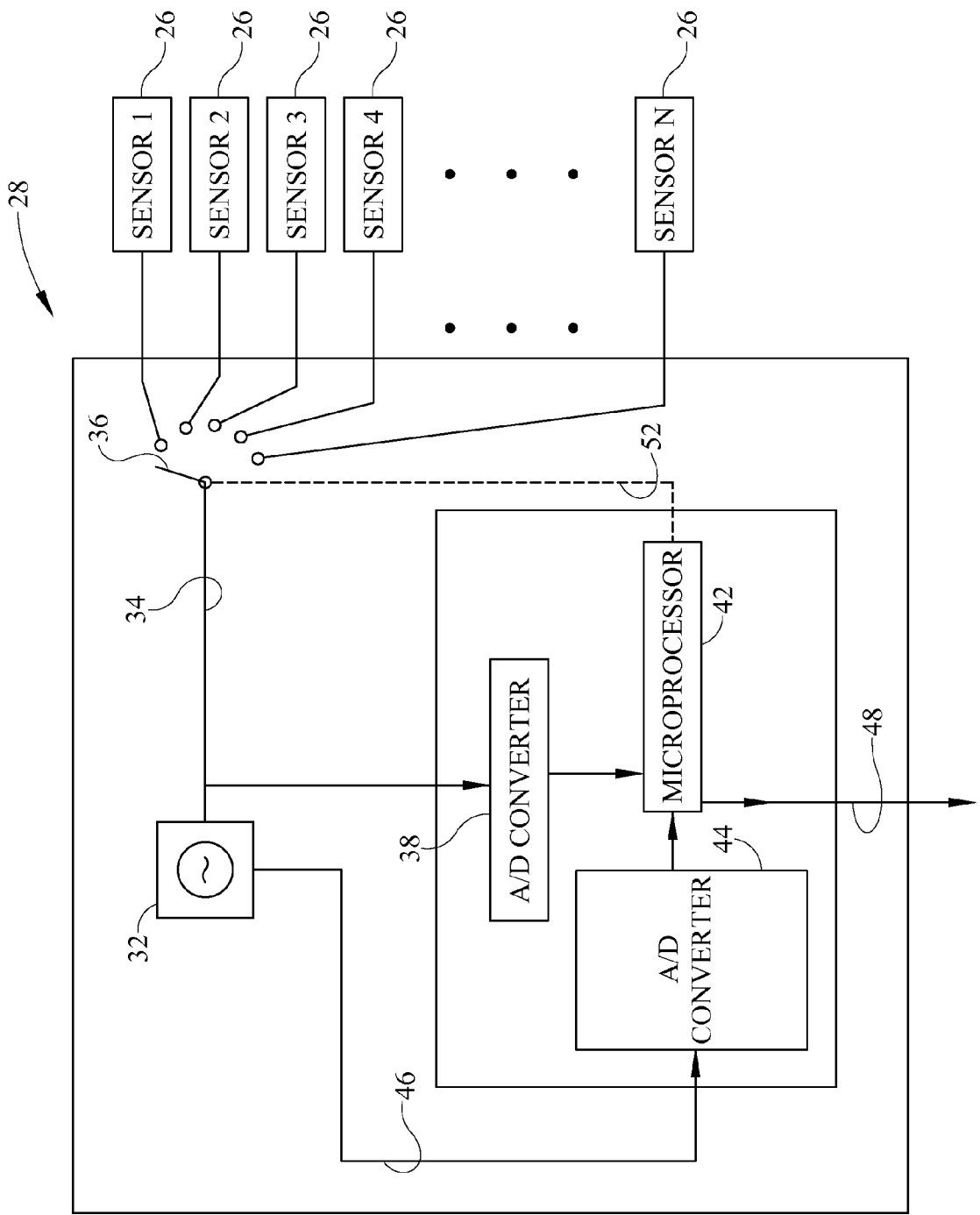
FIG. 2 is a schematic diagram of the diagnostic apparatus or system of FIG. 1.

Referring additionally to FIG. 2, The bed also includes a diagnostic apparatus 28 for assessing the health status of the sensors 26. The diagnostic system includes an analog signal source 32 and a communication path 34 for placing the signal source in communication with one or more sensors of interest 26. The system includes a switch 36 or other means for selectively placing the signal source in communication with the sensor of immediate interest. When the switch is closed, an analog to digital (A-D) converter 38 is also placed in communication with the sensor of interest. A digital processor 42 is connected to both the A-D converter 38 and to a second A-D converter 44. The second A-D converter is also connected to the signal source by a second communication path 46.

The processor 42 has access to one or more complex impedance profiles. A complex impedance profile represents the expected complex impedance amplitude of a sensor of interest when the sensor is excited by a signal from the signal source. As used herein, the phrases "complex impedance", "impedance" and variants thereof refer to impedance having at least a capacitive or inductive component. If all the sensors are expected to have the same complex impedance amplitude (for example if all the sensors are of the same design and are installed in similar ways and in similar environments) a single complex impedance profile will suffice for all the sensors. To the extent the sensors of interest are expected to have different impedance amplitudes (e.g. due to being of differing designs and/or being installed in different environments) the processor will ordinarily have access to one profile for each different expected sensor impedance amplitude.

The processor also has access to an algorithm or method for analyzing the complex impedance of a sensor of interest relative to its expected complex impedance (i.e. to its impedance profile) and for generating, in response to the analysis, a status signal 48 indicating the status of the sensor. Example status signals include a signal to power a lamp or a signal useful in producing a status report.

During operation, the signal source 32 generates a varying frequency electrical excitation signal. The excitation signal is alternating, or at least periodic. The signal travels over communication path 46 to the second A-D converter which digitizes the signal and conveys it to the processor. The excitation signal also travels over communication path 34 and excites the sensor of interest at the frequencies generated by the signal source. The excitation of the sensor at varying frequencies is referred to herein as a frequency sweep. A-D converter 38 digitizes the voltage signal representative of the impedance of the sensor and conveys the digitized signal to the processor. The processor analyzes the complex impedance amplitude of the excited sensor relative to its impedance profile and, in response to the outcome of the analysis, generates output signal 48. The processor also monitors the progress of the frequency sweep by observing the excitation signal arriving from the second A-D converter. At the conclusion of each frequency sweep the processor issues a command over signal path 52 to advance the switch to its next position thereby successively placing the signal source 32 in communication with the next sensor of interest so that the entire complement of sensors of interest can be evaluated.

Figure 3:
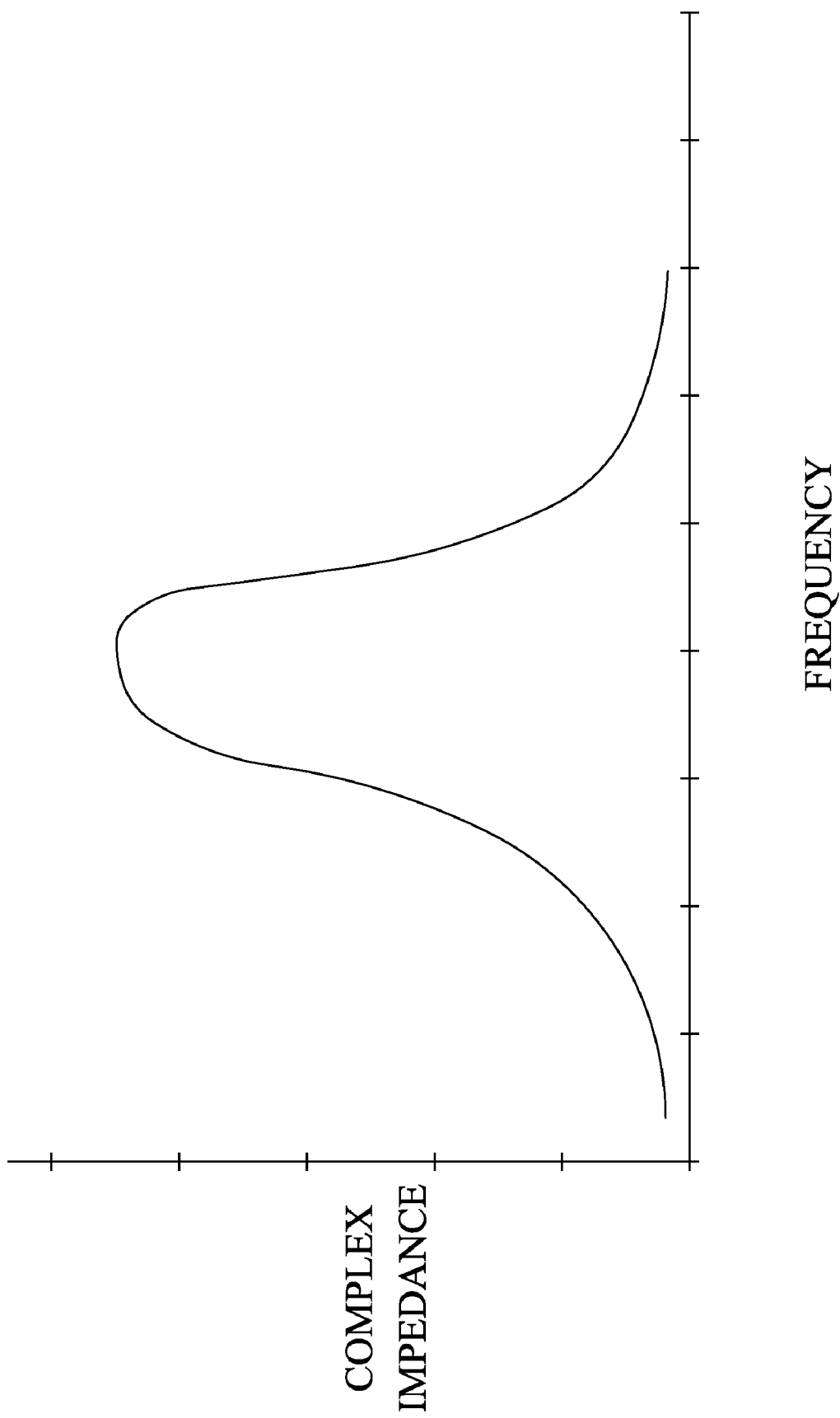
FIG. 3 is a graph illustrating complex impedance amplitude versus excitation frequency for a typical piezoelectric sensor in an unconstrained state.
Figure 4:
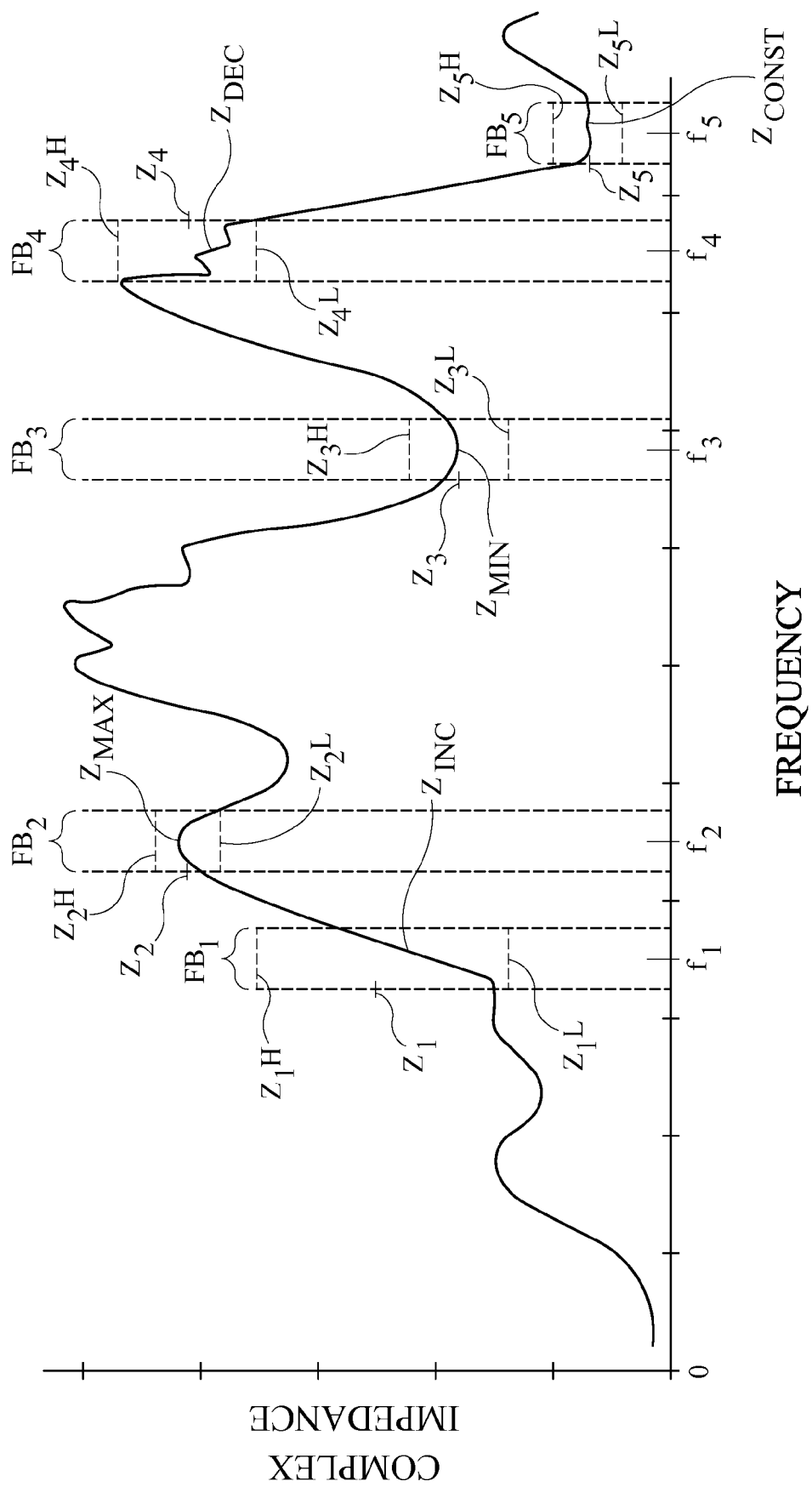
FIG. 4 is a graph illustrating complex impedance amplitude versus excitation frequency for a typical piezoelectric sensor in an installed condition and also shows complex impedance profiles superimposed on the graph.

The method or algorithm used by the processor is understood by first considering the graphs of FIGS. 3 and 4. Both graphs illustrate the amplitude of the complex impedance of an acceptable reference sensor excited by a varying frequency test signal. The graphs of FIGS. 3 and 4 are merely illustrative of the underlying principles, i.e. they do not purport to show the impedance of an actual sensor. FIG. 3 illustrates the intrinsic impedance amplitude versus excitation frequency of a typical unconstrained piezoelectric sensor, i.e. a sensor in an environment where it's mechanical response, and therefore its electrical impedance, are substantially unaffected by external influences. By contrast, FIG. 4 illustrates the impedance amplitude versus excitation frequency of the same sensor in an installed condition, for example installed on a hospital bed as described above. In the installed condition the mechanical response of the sensor, and therefore its electrical impedance, are affected by influences such as physical contact with other components of the bed. The impedance versus frequency relationship can be established empirically by subjecting an actual, installed acceptable sensor to an actual test signal, however it may also be possible to establish the relationship by other means such as developing an accurate mathematical model of the sensor in its installed state.

Continuing to refer to FIG. 4, the complex impedance profile of the acceptable sensor is established by identifying reliably discernible characteristic features of the relationship between complex impedance amplitude and excitation frequency. Such features might include the local maximum Z-MAX occurring at frequency f2, the local minimum Z-MIN occurring at frequency f3, the generally increasing amplitude Z-INC at frequency f1, the generally decreasing amplitude Z-DEC at frequency f4 and the generally constant amplitude Z-CONST at frequency f5. Referring to an amplitude as "generally" increasing, decreasing or constant accounts for the possibility that local peaks or valleys, as seen in frequency band FB4 or other inconsequential deviations may be present without affecting the overall gradient (increasing, decreasing or constant) of the impedance versus frequency relationship. As a practical matter, acceptable manufacturing and installation inaccuracies affect the actual performance of any given installed sensor, and test equipment limitations affect the ability to accurately define both the expected relationship of FIG. 4 and the actual behavior of a sensor of interest. Accordingly, frequency band FB2, centered on f2 and bounded by an upper frequency and a lower frequency, is the frequency band within which local maximum Z-MAX is expected to occur. Similar frequency bands FB1, FB3, FB4 and FB5 are defined for Z-INC, Z-MIN, Z-DEC, and Z-CONST.

In addition to establishing the frequency band in which a particular characteristic feature of the impedance amplitude versus frequency relationship is expected to occur, it may also be desirable to establish the expected amplitude itself. For example, not only is the impedance amplitude expected to be generally increasing in frequency band FB1, but the amplitude itself is expected to have a value of about Z1. More specifically, the amplitude is expected to have a value no lower than about Z1L at the lower frequency side of band FB1 and no higher than about Z1H at the higher frequency side of the band. Similarly, the impedance amplitude in frequency band FB4 is expected to be about Z4, specifically no more than about Z4H at the lower frequency side of the band and no less than about Z4L at the higher frequency side of the band. The value of the maximum in frequency band FB2 is expected to be about Z2, specifically between about Z2L and Z2H; the value of the minimum in frequency band FB3 is expected to be about Z3, specifically between about Z3L and Z3H; the value of the minimum in frequency band FB5 is expected to be about Z5, specifically between about Z5L and Z5H. Moreover, the characteristic feature of the impedance amplitude in frequency bands FB1, FB3 and FB5 can instead be defined as a slope, plus or minus an acceptable tolerance.

Figure 5:
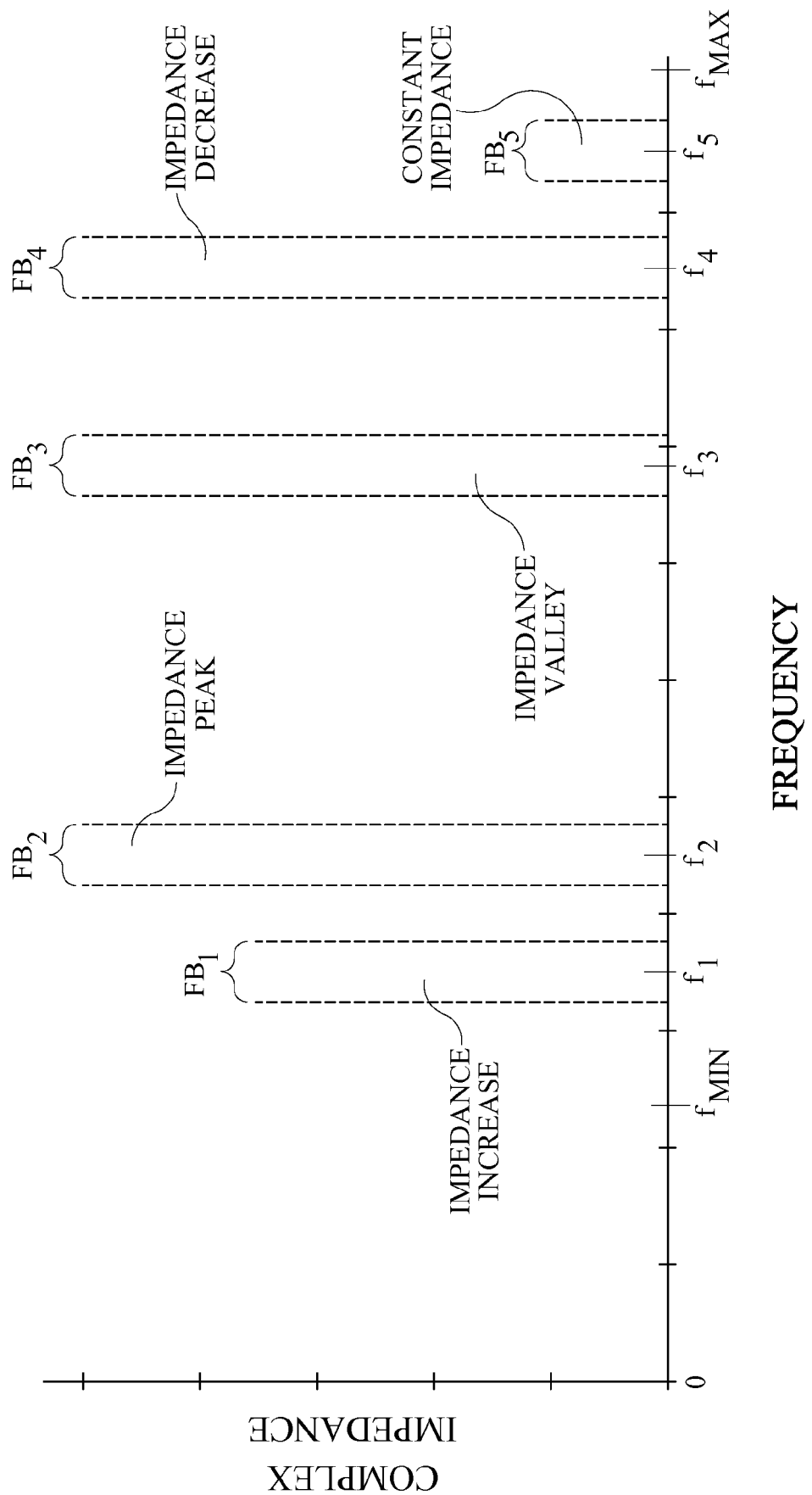
FIG. 5 is a graph similar to FIG. 4 showing a complex impedance profile defined by frequency bands of FIG. 4.
Figure 6:
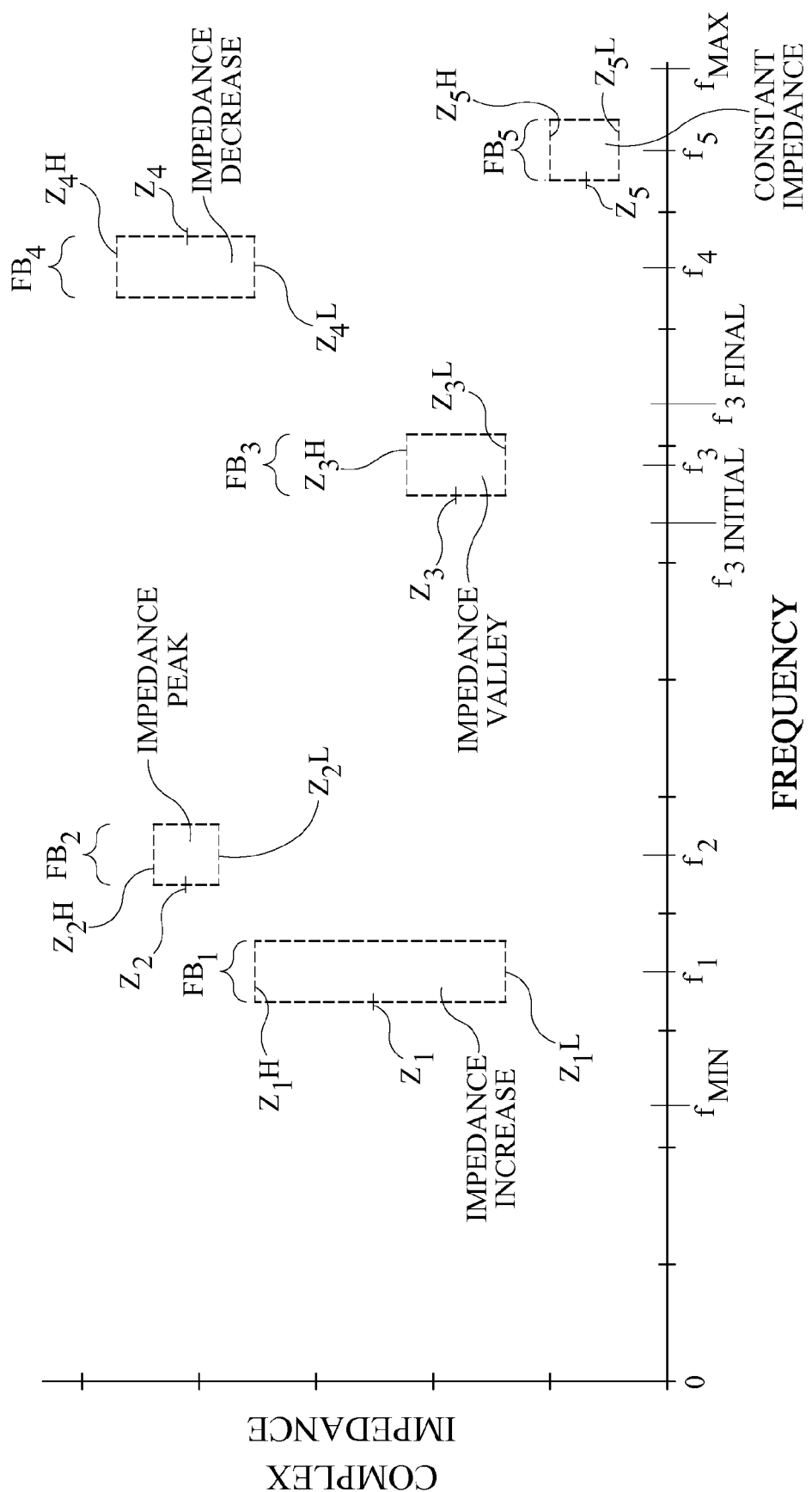
FIG. 6 is a graph similar to that of FIG. 5 showing a refined complex impedance profile defined by impedance-frequency cells.

FIGS. 5 and 6 show the complex impedance profiles described above. Both illustrations are based on FIG. 4 but with the impedance amplitude versus frequency relationship having been omitted. FIG. 5 shows that the complex impedance of the sensor is expected to exhibit certain characteristic features, namely a local maximum, a local minimum, a general increase, a general decrease, or a constant amplitude in each of five frequency bands. FIG. 6 shows the refinement of also defining the range of impedance amplitude expected within each frequency band. As noted above, the refinement in bands FB1, FB3 and FB5 can be expressed as a slope, plus or minus a tolerance.

Figure 7:
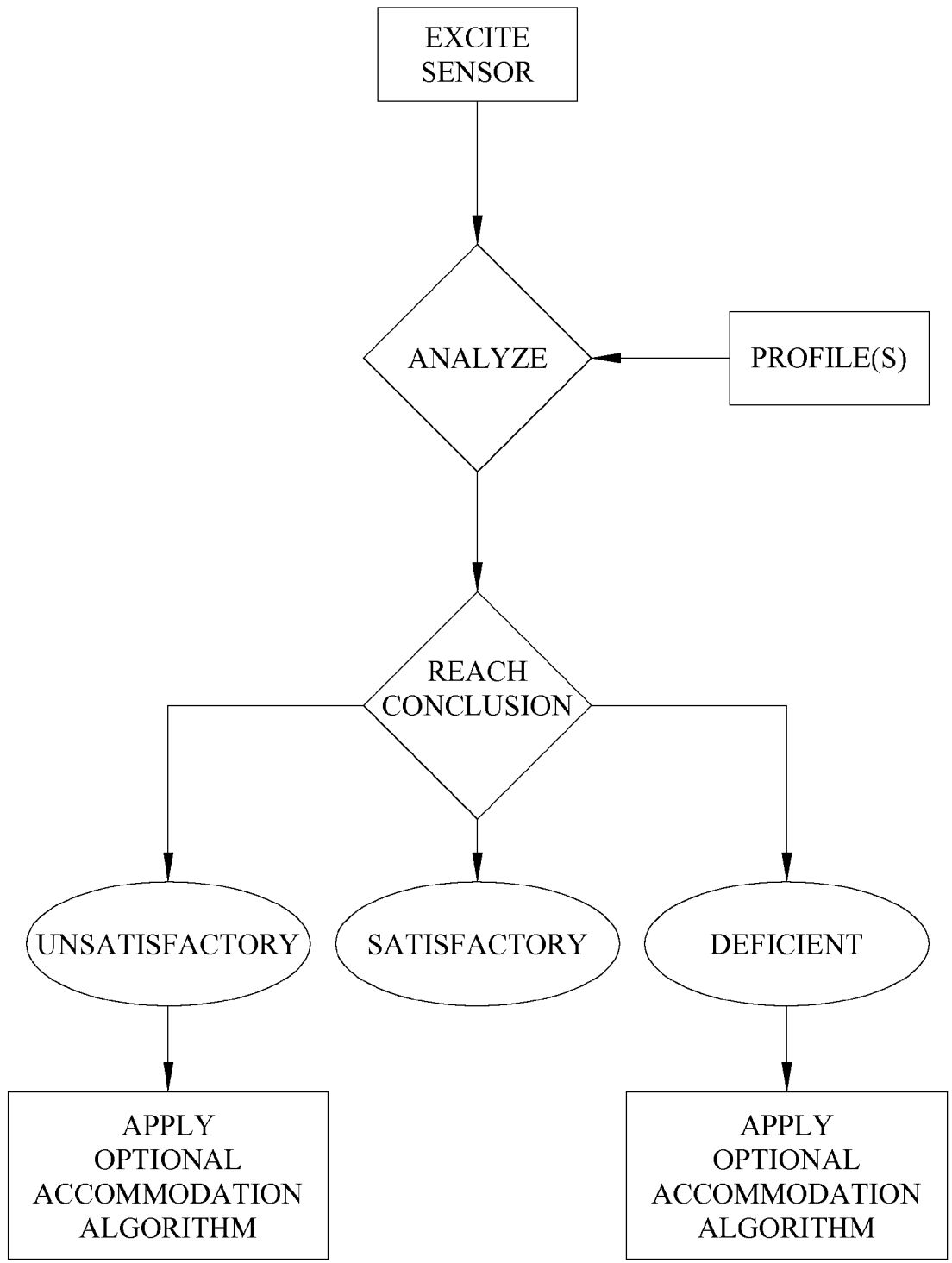
FIG. 7 is a block diagram showing an exemplary method for assessing the status of a piezoelectric sensor of interest.

FIG. 7 is a block diagram showing an exemplary method for assessing the status of a piezoelectric sensor of interest. The method presumes that the complex impedance profile expected to be exhibited by an acceptable sensor has been established, for example as described above. The assessment begins by performing a frequency sweep to excite the sensor with a periodic, varying frequency excitation signal. The excitation signal is correlatable to the test signal used to establish the complex impedance profile. That is, the excitation signal is one that will cause a satisfactory sensor of interest to exhibit the impedance amplitude of the impedance profile or a predictable variation thereof. For example, the amplitude of the excitation signal may be a constant multiple of the amplitude of the test signal. The multiplicative constant can be greater or less than 1.0.

The frequency sweep may be carried out across a broad spectrum of frequencies, e.g. from fMIN to fMAX of FIGS. 5 and 6, encompassing all of the frequency bands. Alternatively, the frequency sweep may comprise multiple mini-sweeps each encompassing an individual frequency band. The encompassing frequencies of a mini-sweep extend to a frequency below the lower frequency boundary of the band and a frequency higher than the upper frequency boundary of the band. For example in frequency band FB3 the encompassing frequencies include and extend between F3-INITIAL and F3-FINAL.

The method then analyzes the complex impedance of the excited sensor relative to the complex impedance profile. The analysis comprises determining if, for each frequency band of interest, the expected impedance amplitude feature (a local maximum, a local minimum, a general increase, a general decrease, a generally constant amplitude, or any of the foregoing including an associated amplitude range) occurs in the frequency band where its presence is expected. The method looks for one and only one of the defining characteristics expected in each frequency band. If the expected feature is present, the outcome of the analysis is "true". If the expected feature is not observed, or is observed at a frequency outside the frequency boundaries of the frequency band, the outcome of the analysis is "false".

The method then reaches a conclusion about the status of the sensor based on the outcome of the analysis. The step of reaching a conclusion may follow various rules. In a stringent variant of the method, the complex impedance profile for a sensor includes N frequency bands. The method concludes that the sensor is satisfactory only if the outcome of the analysis is true for all the frequency bands of interest. The method concludes that the sensor is unsatisfactory if the outcome of even one of the analyses is false. Alternatively, in some applications it may be acceptable to conclude that the sensor is deficient (not performing as expected, but nevertheless performing well enough to be of some value) if even one of the analysis outcomes is false.

In another, less stringent variant of the method, the complex impedance profile for a sensor includes N frequency bands, but the method concludes that the sensor is satisfactory if the outcome of the analysis is true for any M (M less than N) of the N frequency bands of interest. The method concludes that the sensor is, at best, deficient if the outcome of the analysis is true for fewer than M of the frequency bands. The method concludes that the sensor is unsatisfactory if the outcome of the analysis is true for fewer than P of the frequency bands where P is less than M−1. The method concludes that the sensor is deficient (in contrast to deficient at best) if the analysis outcome is true for more than P but fewer than M of the frequency bands.

Another variant of the conclusory step is similar to the less stringent variant except that the M frequency bands are specified bands rather than any M of the N bands. For example, there may be four frequency bands of interest (N=4) centered at frequencies f1, f2, f3 and f4, and it may be required that the outcome of the analysis be true in bands f1, f2 and f4 in order to conclude that the sensor is satisfactory. A true outcome for any other combination of three frequency bands would not support a conclusion that the sensor is satisfactory. However if the analysis outcome were true in all the frequency bands, the user may be justified in assigning greater confidence to the conclusion that the sensor is satisfactory. Independent of the stringency of the test, confidence can also be improved by using a larger quantity of bands, by using impedance amplitude criteria in each frequency band (as in FIG. 6 as opposed to than FIG. 5), and by judiciously selecting the impedance amplitude feature or features used as criteria.

In many practical applications there will be multiple sensors of interest. The method described above may be repeated for all of the sensors of interest as suggested by the switch 36 of FIG. 2. Sensors of different design, or even sensors of the same design subjected to different installed environments, will ordinarily require the use of a profile representative of that sensor in its installed environment. The steps of exciting the sensors, analyzing their behavior and reaching conclusions about their status need not be carried out for each sensor before proceeding to another sensor. Instead, the exciting step can be carried out for all sensors of interest and the impedances can be held in a memory. The analysis can then be done for all the sensors and finally the conclusion can be formed for all the sensors.

Figure 8:
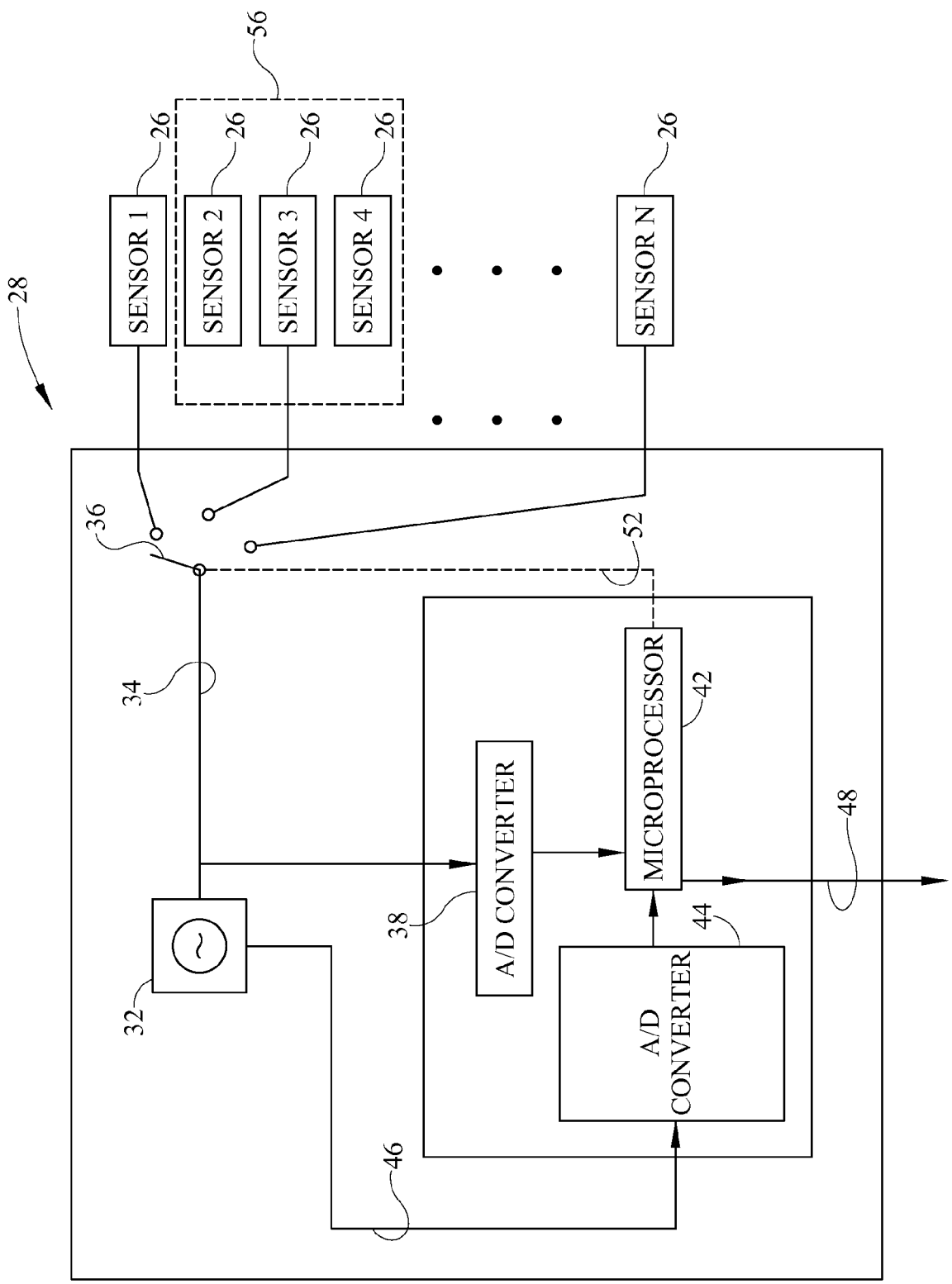
FIG. 8 is a view similar to that of FIG. 2 showing a group of sensors treated as a single sensor.

Referring to FIG. 8, the method can be applied to groups of sensors treated as a single sensor. In FIG. 8 the three sensors within the broken line border 56 form a unit that can, if desired, be treated as a single sensor. The step of establishing the complex impedance profile would be carried out on the unit as a whole, as would the exciting, analyzing and reaching steps. The grouped sensor approach does not, of course, readily reveal which of the grouped sensors is malfunctioning.

The method described above teaches exciting each sensor across a spectrum of frequencies that extend below and above the frequency at which the characteristic feature of the impedance amplitude is expected to occur (e.g. from F3-INITIAL to F3-FINAL for band FB3 of FIG. 4). This reflects the belief that even an unsatisfactory sensor will exhibit the qualitative behavior (e.g. a local minimum, local maximum, increasing amplitude, decreasing amplitude or constant amplitude) and may even exhibit the anticipated impedance amplitude, but will do so at a frequency higher or lower than expected. Alternatively, the frequency sweep may be restricted by, for example, conducting mini-sweeps confined to the N frequency bands. The outcome of the analysis step would then be true if the characteristic feature were present in the band and false if the feature were not present. This latter method is believed to be less useful than the former method. It may also be useful to excite a sensor at a single discrete frequency rather than across a spectrum of frequencies to detect short circuits and open circuits.

In view of the foregoing, certain additional aspects of the method and system can now be better appreciated.

Although the above description discloses test and excitation signals that have a constant amplitude, test and excitation signals whose amplitudes are a function of frequency may also be used.

In order to illustrate various options, FIGS. 5 and 6 show the use of different types of criteria (minimum, maximum, increasing, decreasing or constant) in each of the five frequency bands. In practice, however, the same type of criterion can be used in all the frequency bands.

FIG. 7 shows an optional step that may be carried out if the method concludes a sensor is deficient or unsatisfactory. The optional step accommodates or compensates for the deficient or unsatisfactory sensor, for example by substituting a synthesized signal for the actual output of the sensor identified as deficient or unsatisfactory.

Although this disclosure refers to specific embodiments, it will be understood by those skilled in the art that various changes in form and detail may be made without departing from the subject matter set forth in the accompanying claims.

I claim:

1. A method for assessing the status of a piezoelectric sensor of interest, comprising:
    establishing a complex impedance profile expected to be exhibited by an acceptable sensor subjected to a test signal;
    exciting the sensor of interest with a periodic excitation signal correlatable to the test signal, the sensor of interest being located within a mattress at a position about midway between an upper surface and a bottom surface of the mattress, or lower, and being coupled to a person supported on the mattress by way of a path traversing through solid phase material or liquid phase material without crossing into a substantially gaseous phase material, the entirety of a space defined between the sensor and the person being filled with the solid phase or liquid phase material;
    analyzing the complex impedance of the excited sensor relative to the complex impedance profile; and
    reaching a conclusion about the status of the sensor of interest based on the analysis.

2. The method of claim 1 wherein the step of establishing the complex impedance profile comprises subjecting an actual acceptable sensor to an actual test signal.

3. The method of claim 1 wherein the test signal and the correlatable excitation signal each have an amplitude component, the amplitude of one of the signals being a constant multiple of the amplitude of the other of the signals.

4. The method of claim 1 wherein the sensor is a group of sensors.

5. The method of claim 1 wherein the sensor is one of several sensors and the exciting, analyzing and reaching steps are all carried out for a single sensor before proceeding to another of the several sensors.

6. The method of claim 5 wherein all of the several sensors have the same complex impedance profile.

7. The method of claim 1 wherein the sensor of interest is coupled to a frame of a patient care bed.

8. The method of claim 1 wherein the complex impedance comprises a resistive component, and either a capacitive component or an inductive component.

9. The method of claim 1 wherein:
    the input signal and the excitation signal are constant amplitude alternating signals;
    the complex impedance profile comprises a complex impedance amplitude characteristic expected to be present in one or more frequency bands of interest, each frequency band being defined by a lower frequency and an upper frequency;
    the step of exciting the sensor of interest comprises exciting the sensor of interest at one or more frequencies corresponding to each of the frequency bands of interest;
    the step of analyzing comprises determining whether or not, for each frequency band of interest, the impedance amplitude characteristic occurs within the frequency band of interest.

10. The method of claim 9 wherein the expected impedance amplitude characteristic for each frequency band of interest is one and only one of the characteristics set forth below:
    1) a local maximum amplitude;
    2) a local maximum amplitude falling within an associated amplitude range;
    3) a local minimum amplitude;
    4) a local minimum amplitude falling within an associated amplitude range;
    5) a generally decreasing amplitude;
    6) a generally decreasing amplitude falling within an associated amplitude range;
    7) a generally increasing amplitude;
    8) a generally increasing amplitude falling within an associated amplitude range;
    9) a generally constant amplitude; and
    10) a generally constant amplitude falling within an associated amplitude range
    the associated amplitude range being defined by a lower amplitude and an upper amplitude for each frequency band.

11. The method of claim 10 wherein the analyzing step employs the same impedance amplitude characteristic for all the frequency bands of interest.

12. The method of claim 9 wherein the step of reaching a conclusion comprises:
    concluding that the sensor is satisfactory if the outcome of the analyzing step is true for all the frequency bands of interest.

13. The method of claim 12 wherein the step of reaching a conclusion comprises:
    concluding that the sensor is deficient if the outcome of the analyzing step is false for at least one of the frequency bands of interest.

14. The method of claim 12 wherein the step of reaching a conclusion comprises:
    concluding that the sensor is unsatisfactory if the outcome of the analyzing step is false for at least one of the frequency bands of interest.

15. The method of claim 9 comprising N frequency bands of interest and wherein the step of reaching a conclusion comprises:
    concluding that the sensor is satisfactory if the outcome of the analyzing step is true for at least M of the N the frequency bands of interest where M<N.

16. The method of claim 15 wherein the step of reaching a conclusion comprises:

concluding that the sensor is deficient if the outcome of the analyzing step is true for fewer than M of the frequency bands of interest.

17. The method of claim 16 wherein the step of reaching a conclusion comprises:

concluding that the sensor is unsatisfactory if the outcome of the analyzing step is true for fewer than P of the frequency bands of interest where P<M-1.

18. The method of claim 15 wherein the M frequency bands are specified frequency bands.

19. The method of claim 9 wherein a spectrum of frequencies are employed in each of the frequency bands.

20. The method of claim 9 wherein the analyzing step employs the same impedance amplitude characteristic for all the frequency bands of interest.

21. A system for evaluating the status of one or more piezoelectric sensors of interest comprising:

an analog signal source;

a communication path for placing the signal source in communication with the sensor of interest thereby enabling an excitation signal from the signal source to excite the sensor, the sensor of interest being located within a mattress at a position about midway between an upper surface and a bottom surface of the mattress, or lower, and being coupled to a person supported on the mattress by way of a path traversing through solid phase material or liquid phase material without crossing into a substantially gaseous phase material, the entirety of a space defined between the sensor and the person being filled with the solid phase or liquid phase material;

means for digitizing a complex impedance exhibited by the excited sensor;

a processor having access to a complex impedance profile representing an expected complex impedance of the excited sensor and also having access to an algorithm for analyzing digitized complex impedance relative to the complex impedance profile, the processor being capable of generating a status signal responsive to the analysis.

22. The system of claim 21 wherein the signal source generates a periodic signal.

23. The system of claim 22 wherein the signal source generates an alternating signal.

24. The system of claim 21 wherein the communication path includes means for successively placing the signal source in communication with two or more of the sensors of interest.

25. The system of claim 24 including a signal path from the signal source to the processor for informing the processor to advance the means from a sensor of interest to another sensor of interest.

26. The system of claim 21 wherein the complex impedance comprises a resistive component, and either a capacitive component or an inductive component.

* * * * *